(12) United States Patent
Sevrain

(10) Patent No.: US 8,992,588 B2
(45) Date of Patent: Mar. 31, 2015

(54) SPRING-ASSISTED CRANIAL CLAMP

(75) Inventor: Lionel C. Sevrain, West Palm Beach, FL (US)

(73) Assignee: LERS Surgical, LLC, West Palm Beach, FL (US)

( * ) Notice: Subject to any disclaimer, the term of this patent is extended or adjusted under 35 U.S.C. 154(b) by 1189 days.

(21) Appl. No.: 12/809,145

(22) PCT Filed: Dec. 17, 2008

(86) PCT No.: PCT/US2008/087170
§ 371 (c)(1),
(2), (4) Date: Sep. 28, 2010

(87) PCT Pub. No.: WO2009/085829
PCT Pub. Date: Jul. 9, 2009

(65) Prior Publication Data
US 2011/0034959 A1    Feb. 10, 2011

Related U.S. Application Data

(60) Provisional application No. 61/014,785, filed on Dec. 19, 2007, provisional application No. 61/101,213, filed on Sep. 30, 2008.

(51) Int. Cl.
*A61B 17/84* (2006.01)
*A61B 17/68* (2006.01)

(52) U.S. Cl.
CPC ............ *A61B 17/688* (2013.01); *Y10S 606/903* (2013.01)
USPC .......................................... 606/324; 606/903

(58) Field of Classification Search
CPC .. A61B 17/84; A61B 17/844; A61B 17/8685; A61B 17/688; A61F 2/2875
USPC ............ 606/71, 282, 283, 286, 300, 320, 75, 606/324, 326, 328; 623/17.18, 19; 411/438, 411/439; 24/300, 458
See application file for complete search history.

(56) References Cited

U.S. PATENT DOCUMENTS

| 5,707,373 A | 1/1998 | Sevrain et al. ................... 606/72 |
| 5,800,436 A * | 9/1998 | Lerch ............................. 606/324 |
| 5,916,217 A * | 6/1999 | Manthrop et al. ............... 606/75 |
| 5,964,770 A | 10/1999 | Flomenblit et al. ............. 606/78 |

(Continued)

FOREIGN PATENT DOCUMENTS

| WO | WO 2006/002744 | 1/2006 |
| WO | WO 2007/086901 | 8/2007 |
| WO | WO 2007/146541 | 12/2007 |

OTHER PUBLICATIONS

"CranioFix2, Implant system for refixation of cranial bone flaps after craniotomy," located on www.aesculapusa.com website, downloaded Aug. 22, 2008.

(Continued)

*Primary Examiner* — Michael T Schaper
*Assistant Examiner* — Amy Sipp
(74) *Attorney, Agent, or Firm* — Novak Druce Connolly Bove + Quigg LLP

(57) ABSTRACT

A cranial clamp for attaching a cranial flap to the skull comprises a clamp having a base to be placed against the lamina interna, and a cap acting as a locking member against the lamina externa. The clamp and the cap are linked together by an extension spring within the diploe through a burr hole or along/within the line of a craniotomy.

1 Claim, 10 Drawing Sheets

(56) References Cited

U.S. PATENT DOCUMENTS

| | | | |
|---|---|---|---|
| 6,050,998 A | 4/2000 | Fletcher | 606/74 |
| 6,126,663 A | 10/2000 | Hair | 606/72 |
| 6,187,004 B1* | 2/2001 | Fearon | 606/57 |
| 6,197,030 B1* | 3/2001 | Pham | 606/323 |
| 6,258,091 B1 | 7/2001 | Sevrain et al. | 606/72 |
| 6,302,884 B1* | 10/2001 | Wellisz et al. | 606/86 B |
| 6,379,363 B1* | 4/2002 | Herrington et al. | 606/79 |
| 6,485,493 B1 | 11/2002 | Bremer | 606/70 |
| 6,572,623 B1 | 6/2003 | Birchall et al. | 606/76 |
| 6,589,244 B1 | 7/2003 | Sevrain et al. | 606/72 |
| 6,685,707 B2* | 2/2004 | Roman et al. | 606/916 |
| 6,755,834 B2* | 6/2004 | Amis | 606/916 |
| 7,238,188 B2* | 7/2007 | Nesper et al. | 606/328 |
| 7,361,178 B2* | 4/2008 | Hearn et al. | 606/281 |
| 7,387,633 B2* | 6/2008 | Ahmad et al. | 606/281 |
| 7,867,262 B2* | 1/2011 | Morales et al. | 606/281 |
| 8,206,425 B2* | 6/2012 | Khanna | 606/324 |
| 8,226,694 B2* | 7/2012 | Broaddus et al. | 606/286 |
| 2002/0016593 A1 | 2/2002 | Hearn et al. | 606/72 |
| 2002/0169455 A1* | 11/2002 | Bannerman et al. | 606/99 |
| 2004/0034367 A1 | 2/2004 | Malinowski | 606/129 |
| 2005/0107813 A1* | 5/2005 | Gilete Garcia | 606/151 |
| 2005/0137608 A1 | 6/2005 | Hearn et al. | 606/103 |
| 2008/0051792 A1* | 2/2008 | Gilete Garcia | 606/72 |
| 2008/0200954 A1 | 8/2008 | Tucci | 606/280 |
| 2011/0022098 A1* | 1/2011 | Gilete Garcia | 606/300 |
| 2012/0184999 A1* | 7/2012 | Khanna | 606/281 |

OTHER PUBLICATIONS

Brochure—"Aesculap Neurosurgery, Cranial Fixation Systems," Aesculap, Inc., 2008.
Brochure—"Lorenz® Plating System Neuro, RapidFlap™ SpinDown," Biomet Microfixation, 2007.
PCT International Preliminary Report on Patentability issued in International Application No. PCT/US2008/087170, mailed Jul. 1, 2010.
PCT International Search Report and Written Opinion issued in International Application No. PCT/US2008/087170, mailed Jun. 26, 2009.

* cited by examiner

SPRING-ASSISTED CRANIAL CLAMP

The present application is a national phase application filed under 35 USC §371 from PCT/US2008/087170, filed Dec. 17, 2008, which claims priority to U.S. Provisional Patent Application Ser. No. 61/014,785, filed Dec. 19, 2007, and U.S. Provisional Patent Application Ser. No. 61/101,213, filed Sep. 30, 2008, all of which applications are incorporated by reference herein in their entirety.

FIELD OF THE INVENTION

This invention relates to a fastener for quickly and securely fastening a cranial bone flap to the surrounding bone, and more particularly to adjustable fasteners that allow for post-operative cerebral edema and intracranial hypertension.

BACKGROUND OF THE INVENTION

When performing surgery on the brain, it is often necessary to perform a craniotomy to provide access to portions of the brain. A craniotomy is a surgical procedure in which a portion of the cranial vault is removed to permit access to the brain. To perform the craniotomy, several burr holes are initially drilled through the skull. A saw is then used to cut the skull along the line of separation connecting the adjoining burr holes, i.e., a craniotomy is performed. The resulting bone cover or cranial flap is subsequently lifted from the underlying dura mater to expose the brain. The bone cover may either be completely removed from the cranium, or folded back on a muscular and/or aponeurotic hinge.

After completion of the procedure on the brain, the bone cover must be re-attached to the skull using either non-resorbable sutures, and more recently using devices that have been developed to help secure the bone cover to the skull such as cranial clamp. See, for example, U.S. Pat. No. 6,258,091 to Sevrain et al., U.S. Pat. No. 6,589,244 to Sevrain et al., U.S. Pat. No. 5,707,373 to Sevrain et al., and U.S. Pat. No. 6,685,707 to Roman et al. (all of which are incorporated by reference herein in their entirety). These fasteners (Rapid Flap™—Walter Lorenz Surgical— or CranioFix™—Aesculap, Stryker—) allow a fast, secure and anatomical repositioning of the bone cover, but realize a rigid fixation which forbids movement of the flap, especially during the post-operative course when a brain swelling may occur.

This inability to expand in case of post-operative swelling can be harmful to the brain in damaging cerebral tissues due to the increase of intracranial pressure (ICP). Similarly, these rigid fixations cannot be used when a decompressive craniotomy (to relieve cerebral edema and intracranial hyperpression following a traumatic brain injury) is performed. Therefore, a dynamic fixation allowing the flap to accommodate swelling while still aligning properly for healing would be desirable.

SUMMARY OF THE INVENTION

It is therefore an aim of the present invention to provide a novel fastener for securely re-attaching a cranial flap to the skull, it is also an aim of the present invention to provide a fastener capable of acting as a dynamic fixation to allow reversible linear displacements of the cranial flap.

Therefore, in accordance with the present invention, there is provided a fastener for attaching a cranial flap to the skull, comprising a clamp having a base to be placed against the lamina interna, and a cap acting as a locking member against the lamina externa, both being linked together by an extension spring within the diploe through a burr hole or along/within the line of craniotomy. Further in accordance with the present invention, there is provided a method for re-attaching a cranial flap to the skull comprising the steps of: (a) positioning the clamps (b) re-positioning the flap (c) securely locking the clamp.

In one embodiment of the invention, there is a cranial clamp for attaching a cranial flap to the skull, comprising: a clamp having a base adapted to be placed against the lamina interna of the skull; and a cap acting as a locking member against the lamina externa of the skull; wherein both the clamp and the cap are linked together by an extension spring within the diploe through a burr hole.

In another embodiment, there is a cranial clamp for attaching a cranial flap to the skull, comprising: a clamp having a base adapted to be placed against the lamina interna of the skull; and a cap acting as a locking member against the lamina externa of the skull; wherein both the clamp and the cap are linked together by an extension spring within the diploe along the line of the edge of the cranial flap.

In an additional embodiment, there is a cranial clamp for attaching a cranial flap to the skull, comprising a spring and a securing member.

In another embodiment there is a method of attaching a cranial flap to the skull, comprising: providing a skull and cranial flap separated by a craniotomy incision; generating a generally oblique tunnel in the skull suitable for entry of an extension apparatus through the tunnel, wherein the direction of the angle of the tunnel is towards the craniotomy incision; generating a generally oblique tunnel in the cranial flap suitable for entry of an extension apparatus through the tunnel, wherein the direction of the angle of the tunnel is towards the craniotomy incision; placing the extension apparatus through the respective tunnels of the skull and flap; and securing the extension apparatus to the skull and flap, respectively. In a specific embodiment, the extension apparatus is a spring or rubber band. In another specific embodiment, the securing step is further defined as screwing the ends of the extension apparatus to the skull and flap, respectively.

In an additional embodiment of the invention, there is a method of attaching a cranial flap to the skull, comprising: providing a skull and cranial flap separated by a craniotomy incision; and securing each end of an extension apparatus to the skull and cranial flap such that the extension apparatus traverses the craniotomy incision in a generally horizontal direction outside the skull (flap and vault). In a specific embodiment, the extension apparatus is a spring or rubber band. In another specific embodiment, the securing step is further defined as screwing the ends of the extension apparatus to the skull and flap, respectively.

From the foregoing disclosure and the following more detailed description of various preferred embodiments it will be apparent to those skilled in the art that the present invention provides a significant advance in the technology of cranial bone flap fixation devices. Particularly significant in this regard is the potential the invention affords for providing a high quality device which can adjust in response to varying physiological conditions. Additional features and advantages of various preferred embodiments will be better understood in view of the detailed description provided below.

Other and further objects, features, and advantages would be apparent and eventually more readily understood by reading the following specification and be reference to the accompanying drawings forming a part thereof, or any examples of the presently preferred embodiments of the invention given for the purpose of the disclosure.

Figure 1:
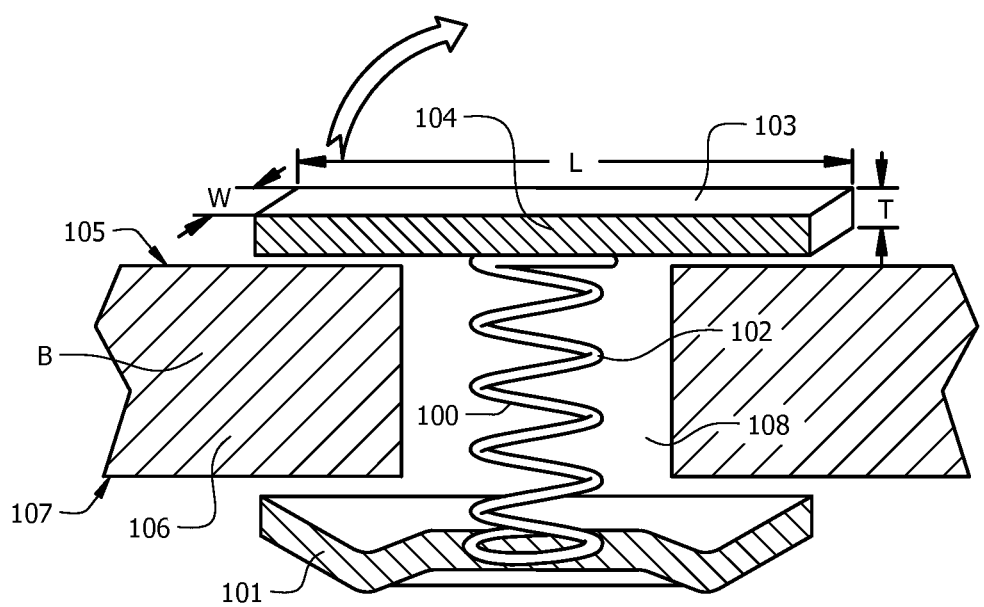
FIG. 1 is a lateral view of a spring-assisted cranial clamp in its locked configuration in accordance with a preferred embodiment.

It should be understood that the appended drawings are not necessarily to scale, presenting a somewhat simplified representation of various preferred features illustrative of the basic principles of the invention. The specific design features of the cranial clamp as disclosed here, including, for example, the specific dimensions of the spring, will be determined in part by the particular intended application and use environment. Certain features of the illustrated embodiments have been enlarged or distorted relative to others to improve visualization and clear understanding, in particular, thin features may be thickened, for example, for clarity of illustration. All references to direction and position, unless otherwise indicated, refer to the orientation illustrated in the drawings.

DETAILED DESCRIPTION OF CERTAIN EMBODIMENTS OF THE INVENTION

It will be readily apparent to one skilled in the art that various embodiments and modifications may be made in the invention disclosed herein without departing from the scope and spirit of the invention.

Unless defined otherwise, technical and scientific terms used herein have the same meaning as commonly understood by one of ordinary skill in the art to which this invention belongs. For purposes of the present invention, the following terms are defined below.

As used herein, the use of the word "a" or "an" when used in conjunction with the term "comprising" in the claims and/or the specification may mean "one," but it is also consistent with the meaning of "one or more," "at least one," and "one or more than one." Some embodiments of the invention may consist of or consist essentially of one or more elements, method steps, and/or methods of the invention. It is contemplated that any method or composition described herein can be implemented with respect to any other method or composition described herein.

It will be apparent to those skilled in the art, that is, to those who have knowledge or experience in this area of technology that many uses and design variations are possible for the cranial clamp disclosed here. The following detailed discussion of various alternative and preferred features and embodiments will illustrate the general principles of the invention with reference to a cranial clamp suitable for use in patients who may be susceptible to post-operative cerebral edema, intracranial hypertension and the like. Other embodiments suitable for other applications will be apparent to those skilled in the art given the benefit of this disclosure.

Figure 8:
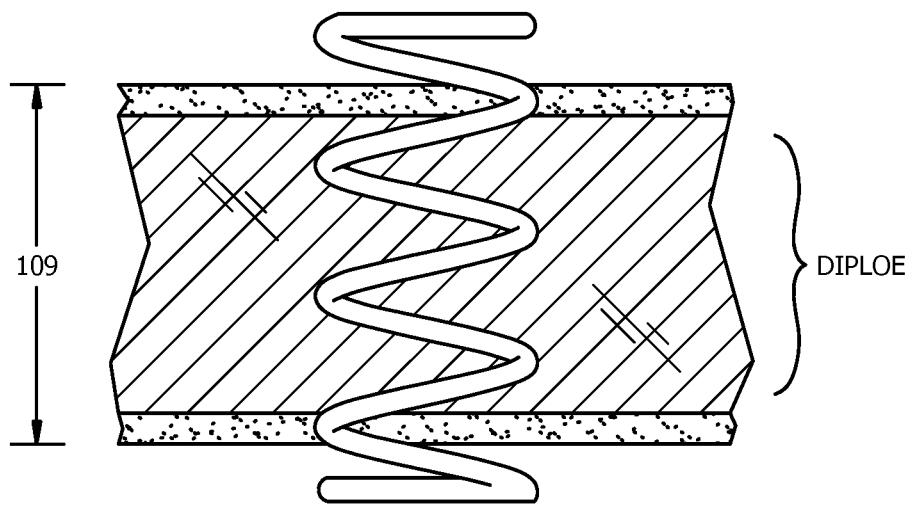
FIG. 8 is a lateral view of an illustration of a particular embodiment of the clamp wherein the spring runs perpendicular within the space between the bone flap and the skull to allow reversible linear displacements of the cranial flap.
Figure 9:
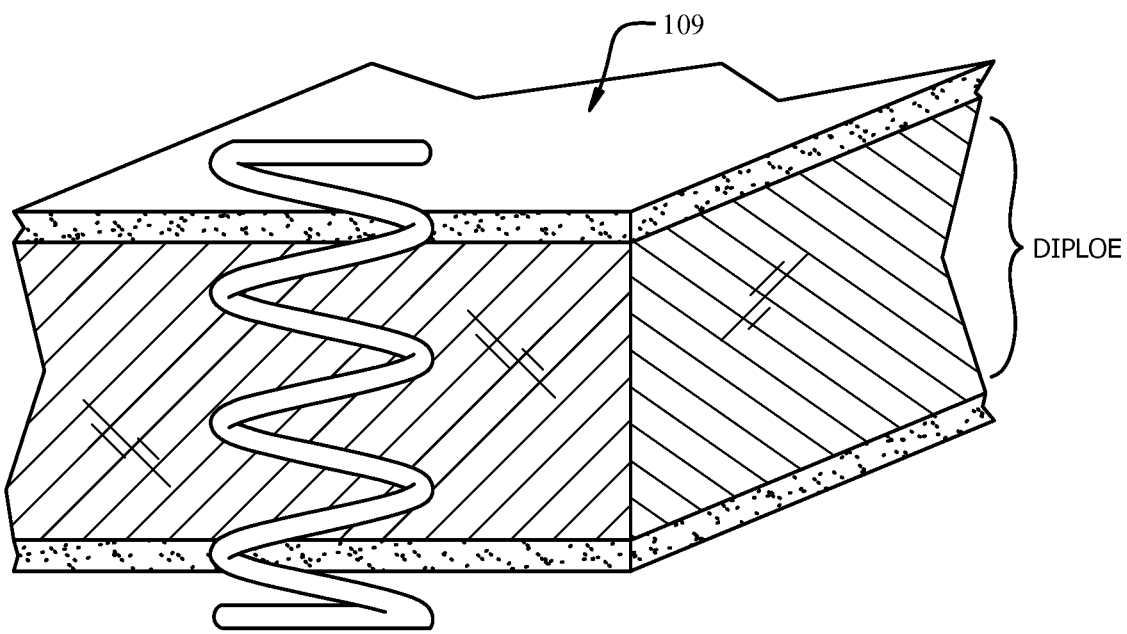
FIG. 9 is another lateral view of the embodiment of the spring-assisted clamp in FIG. 8.
Figure 10:
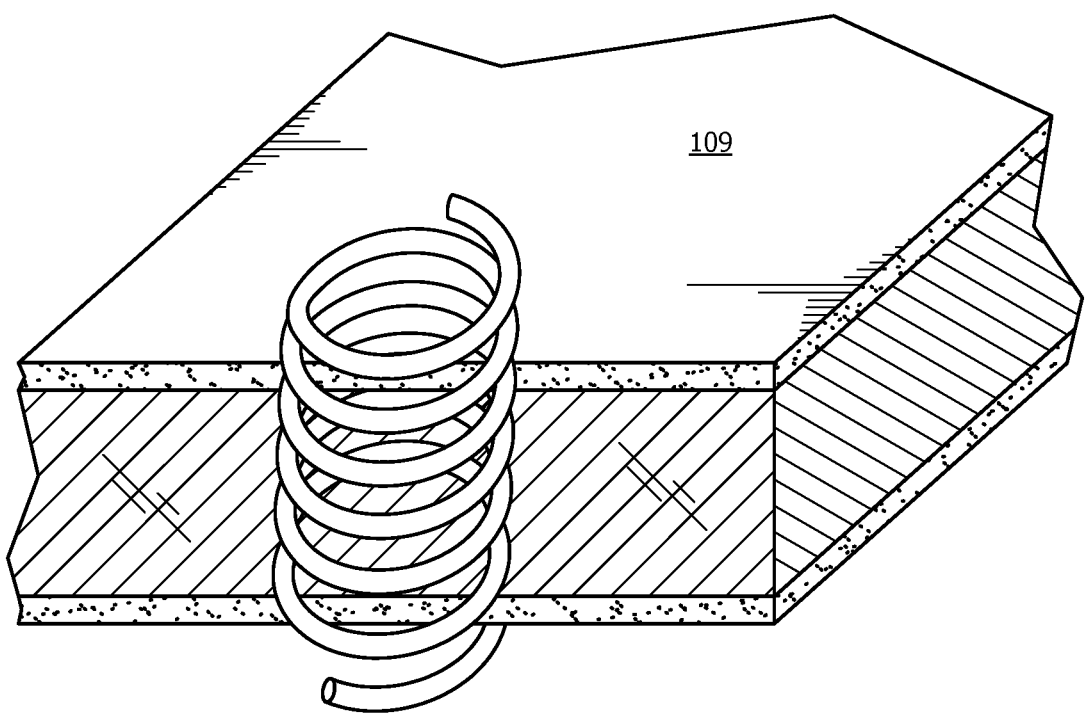
FIG. 10 is a top view of the embodiment of the spring-assisted clamp in FIG. 8.

Referring now to the Figures, in accordance with a preferred embodiment, a cranial clamp 100 is disclosed comprising an anchoring member A and a locking member L. FIG. 1 illustrates a spring-assisted cranial clamp 100 in a locked configuration after implantation within the bone (B). A base 101 is circular and intended to be positioned into the extradural space, between the dura mater and the lamina interna 107. The base preferably has a thin and flat design to avoid the detachment of the dura mater and the compression of the brain and a smooth shape to avoid any tears of the dura mater. Positioning of the spring relative to the cut of the craniotomy is in a generally vertical position relative to the cut of the craniotomy, as illustrated in FIGS. 8-10.

The spring 102 can be, for example, a coil spring. Generally a spring is understood here to mean a mechanical device made by winding a wire around a cylinder, which is typically used to store energy and subsequently release it, or to maintain a force between contacting surfaces. The spring is made of an elastic material formed generally in the shape of a helix which returns to its natural length when unloaded.

The spring 102 preferably has the following characteristics: It is an extension spring e.g. designed to become longer under load. Its turns are normally touching in the unloaded position. When the skull and the flap move apart (edema), the spring resists such movement. Therefore, its stiffness (N/mm), or its inverse, its compliance (mm/N) are set to allow the flap to protrude in case of brain edema, and then line up to the skull after disappearance of the swelling. Given that the physiological intra-cranial pressure (ICP) is measured in millimeters of mercury (mmHg) and, at rest is normally less than 10-15 mmHg, the rate of the spring is preferably set to this value.

The spring length depends of the thickness of the diploe 106. The cranial vault thickness varies from 4 to 5 mm (squamous portion of the temporal bone) through 18 to 20 mm (frontal bone). Preferably a diameter of the spring does not exceed 3 mm when used through the craniotomy line, but can be up to 10 mm when used through the burr hole 108.

Preferably the spring is made of a bio-compatible material such as, but not limited to, Titanium, Stainless Steel, gold, silver, tantalum, etc. The spring may also be made of memory-shaped material or polymer capable of expansion. In these two last cases, the resilient material acts as a spring, e.g. a flexible elastic object used to store mechanical energy, but does not keep necessarily the same helical-shaped wire design.

The cap is a horizontal bar 103 acting as a locking mechanism, its width w is inferior (<2 to 4 mm) to the size of line of craniotomy (gap between the flap and the skull) and its length l is superior (>10 mm) to the size of the line of craniotomy. Preferably the cap has edges which are blunted to avoid any damages to the subcutaneous tissue. The cap has two lateral sides which define a notch 104 intended to receive a prehensile tool. Cap thickness t is a few millimeters to avoid any unaesthetic consequences. The arrow in FIG. 1 indicates a 90° clockwise rotation of the device to line up the bar 103 with the line of craniotomy, and then the flap may be freed.

Figure 2:
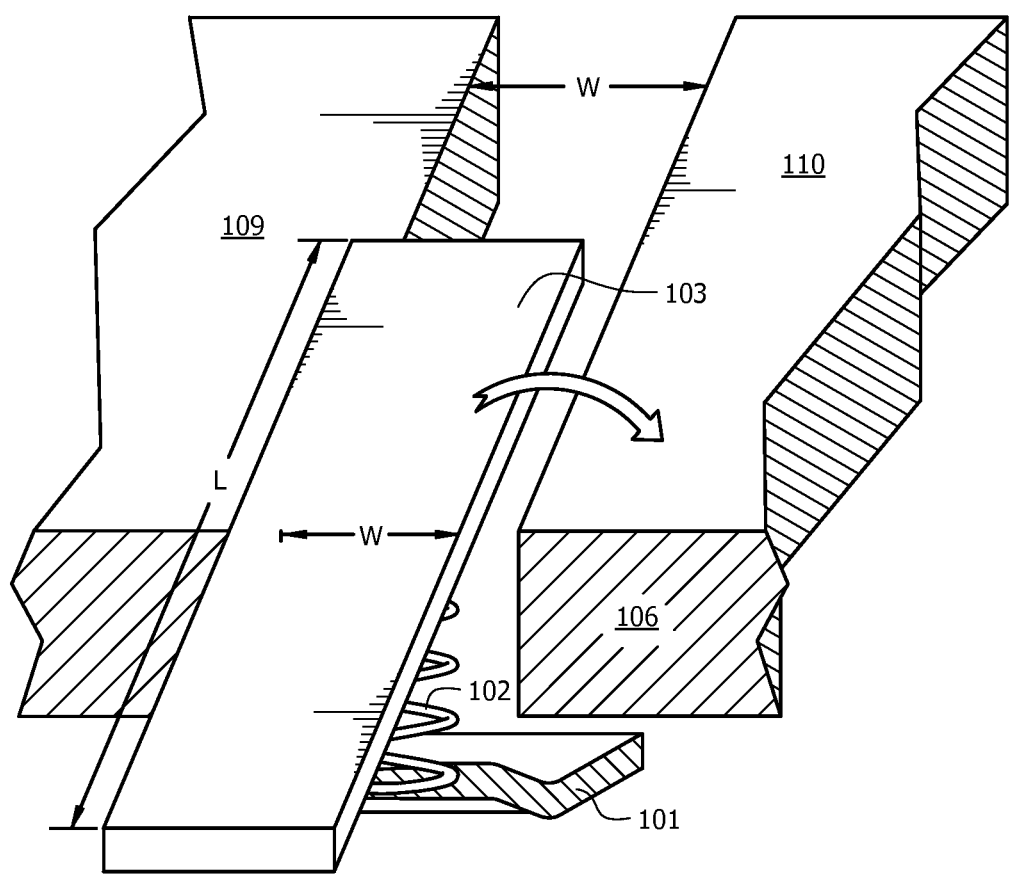
FIG. 2 is a schematic perspective view of a spring-assisted cranial clamp in its unlocked configuration.

FIG. 2 illustrates a spring-assisted cranial clamp 100 in an unlocked configuration. The bar 103 lines up with the line of craniotomy which separates the skull 109 from the flap 110. The bar width w is inferior to the width W of the line of craniotomy (w<W). Its length L is longer than the width W of the line of the craniotomy (L>W). The arrow ** shows a 90° clockwise rotation of the bar 103 to lock the flap 110 by crossing over the line of craniotomy. in addition to the locking function, the bar 103 has also an anti-sinking function. A cerebral atrophy may result of such brain damage and lead to the sinking of the flap 110. The most characteristic sign is the deflection of a small part of the surface (syndrome of the sinking skin flap) with inwardly cranial displacement of the flap which results in a disastrous aesthetic as well as blood flow regulation consequences. The bar 103 opposes to the depression of flap under such hypotensive conditions.

Figure 3:
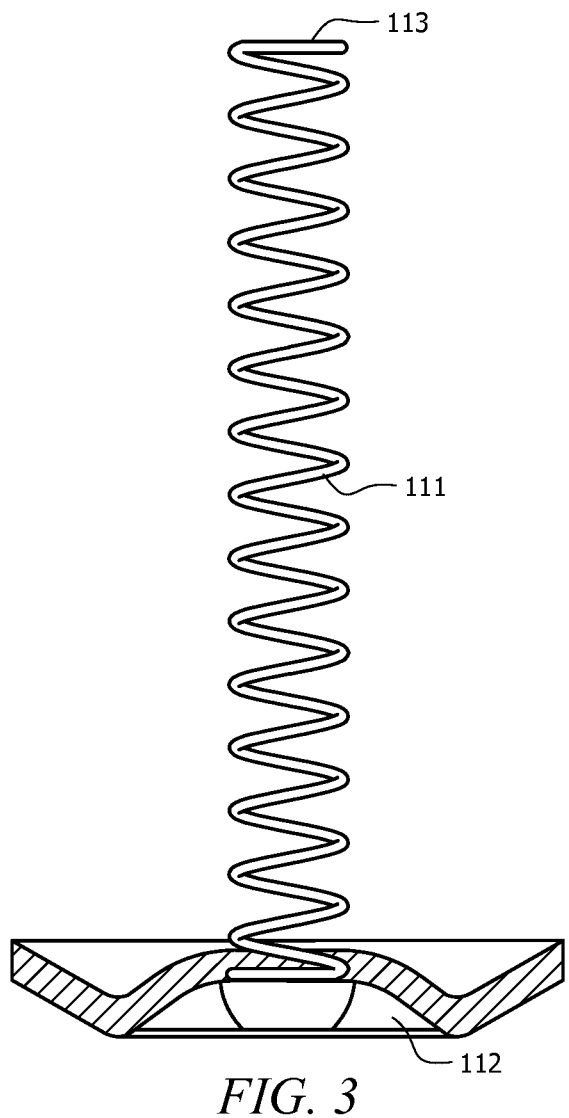
FIG. 3 is a lateral view of another preferred embodiment showing a longer spring and its base.

FIGS. 3-7 disclose a second preferred embodiment. FIG. 3 is a lateral view showing a longer spring 111 and its base 112. In this embodiment, the spring which is still an extension-type spring, differs from the previous embodiment because its length is not set, but will be preoperatively sectioned to the adequate length. The first turn of the spring is the distal end 113.

Figure 4:
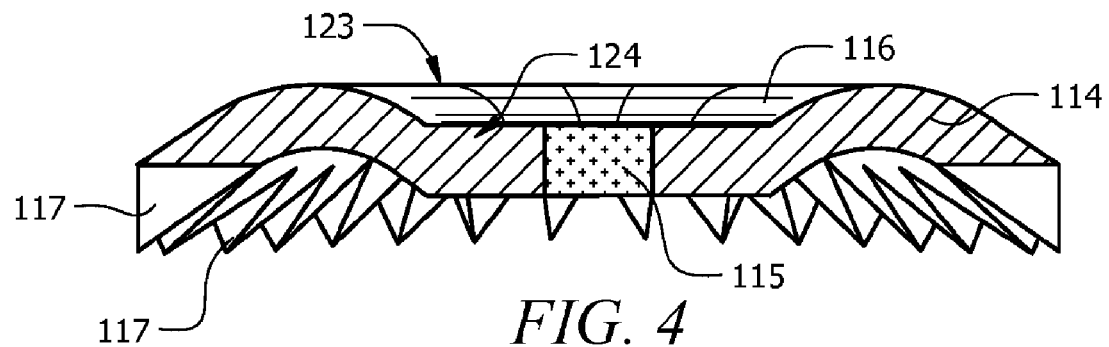
FIG. 4 is a cross-sectional plan view of the cap of the preferred embodiment of FIG. 3.

FIG. 4 is a cross-sectional plan view of the cap 114 of the second embodiment; It differs from the bar 103 by its shape which is no longer a thin bar but a solid disc intended to secure the flap and occlude the burr hole. The cap has an upper face which presents a conical-shaped central recess 116 with an outer wide mouth 123 and an inner narrow end 124 disposed coaxially to a central unthreaded aperture 115 intended to receive the distal end 113 (first turn) of the spring. Then, the cap 114 is spiraled down through its central aperture 115 along the turns of the spring. The lower face of the cap 114 includes a series of radial teeth 117 intended to grip into the lamina externa 105.

Figure 5:
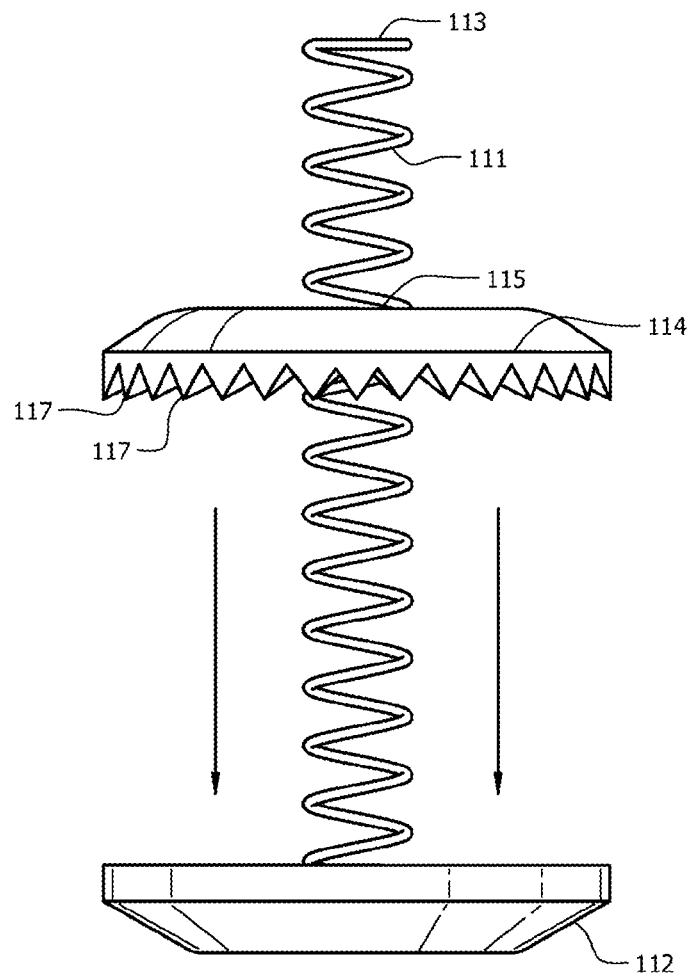
FIG. 5 is a lateral view of the assembly of the preferred embodiment of FIG. 3 when the cap is spiraled down along the turns of the spring.
Figure 6:
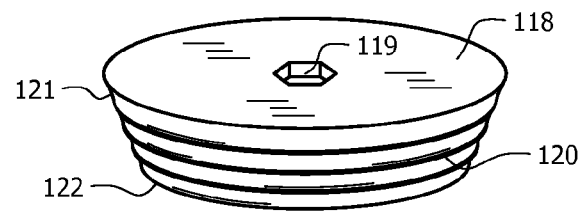
FIG. 6 is a schematic perspective view of the locking member intended to be screwed into the conical-shaped top of the cap.

FIG. 5 is a lateral view of the assembly of the second embodiment when the cap is spiraled down along the turns of the spring. FIG. 6 is a schematic perspective view of the locking member 118 intended to be screwed via threads 120 into the conical-shaped recess 116 of the cap 114. An outer face 121 has a Hex type's socket 119 such that it can be engaged by a Hex (hexagonal) tip fastener like a key or wrench.

An inner face 122 of the locking member is flat. Once the cap 114 has been spiraled down to the lamina externa 105, the unneeded stuck out portion of the spring 111 is sectioned just out of the wide mouth 123 horizontal plan, so that at least one turn of the spring is into the conical-shaped central recess 116 contained between the outer wide mouth 123 and the inner narrow end 124. The locking member 118 is engaged into the conical-shaped central recess 116 and then screwed in until the locking member blocks the turn of the remaining spring. Therefore, the clamp 100 securely attaches the flap 110 to the skull 109, the spring 111 set at the adequate length is locked by the locking member 118 and the assembly is completed.

Figure 7:
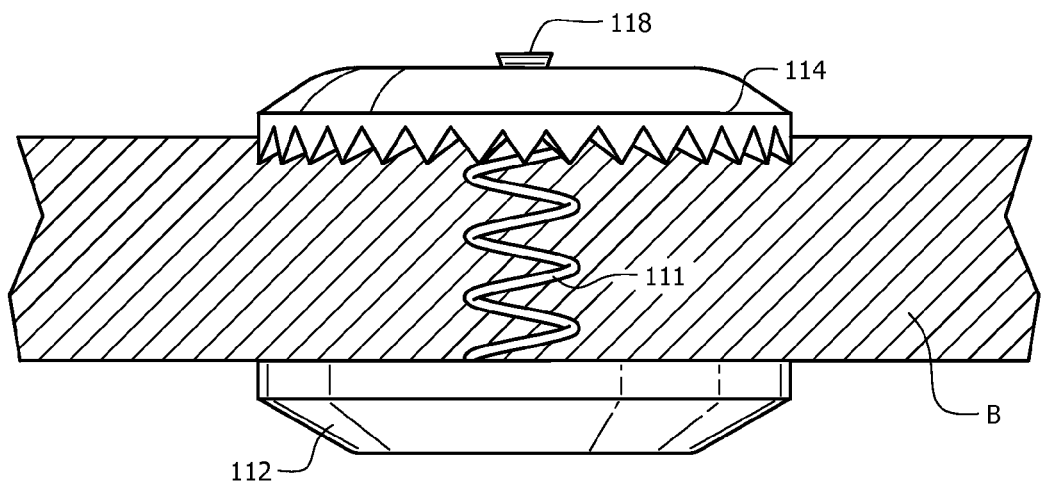
FIG. 7 is a lateral view of the final assembly of the preferred embodiment of FIG. 3 after the cap has been brought down to the bone, the stuck out spring has been cut, and the end securely blocked into the cap with the threaded locking member.

FIG. 7 is a lateral view of the final assembly of the second embodiment after the cap 114 has been brought down to the bone B, the stuck out spring 111 has been cut, and the end securely blocked into the cap 114 with the threaded locking member 118.

Figure 11:
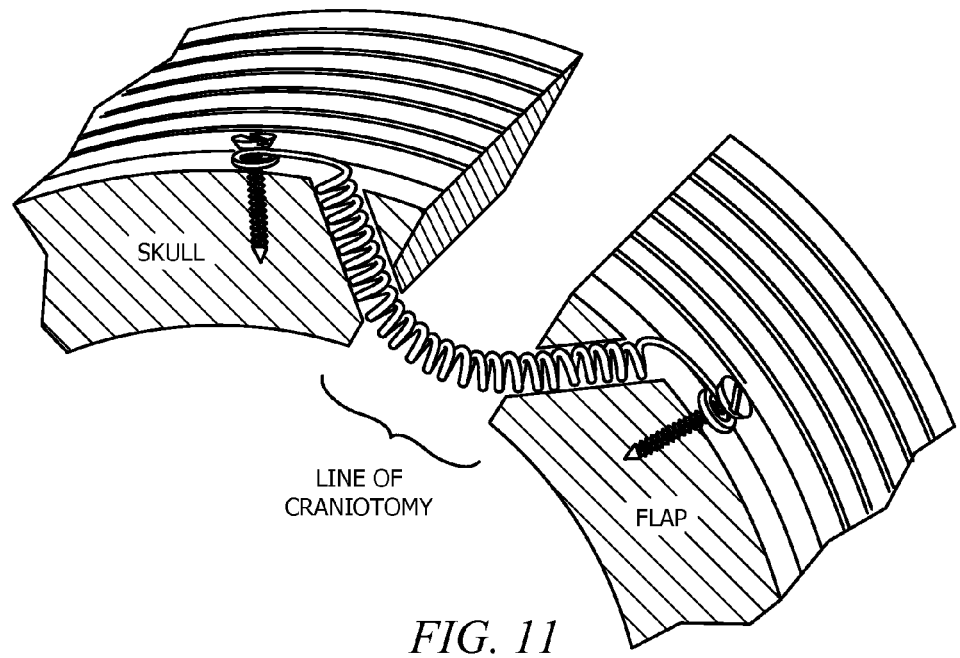
FIG. 11 illustrates one embodiment wherein the spring traverses the cut in a generally oblique manner through the diploe.
Figure 12:
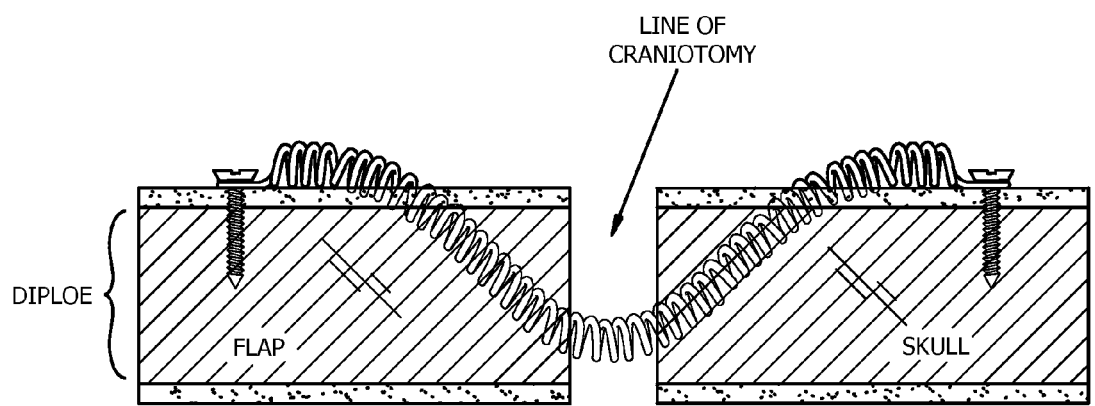
FIG. 12 provides a side view of the clamp embodiment of FIG. 11.
Figure 13:
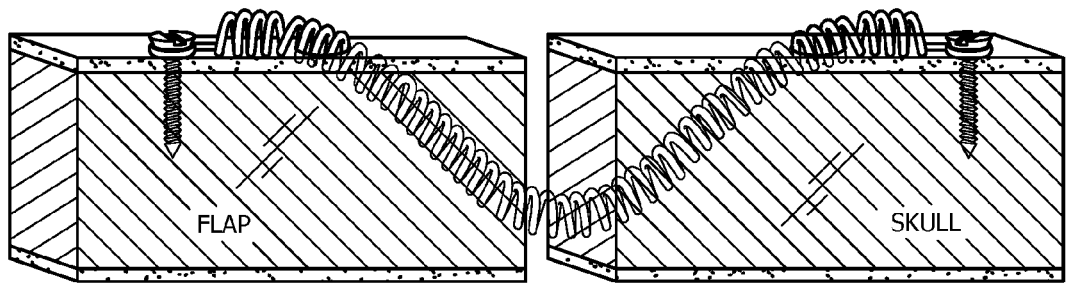
FIG. 13 provides another side view of the clamp embodiment of FIG. 11.
Figure 14:
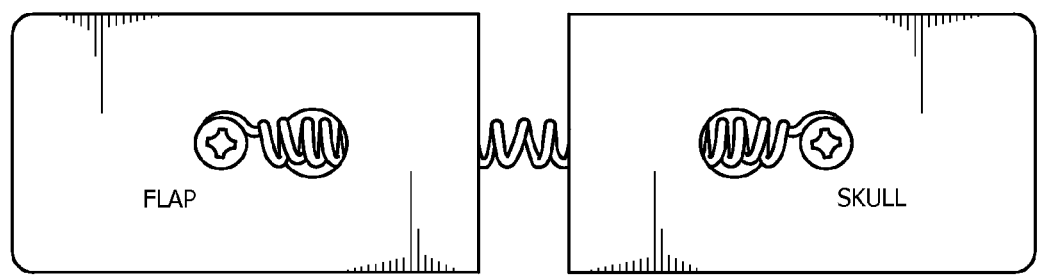
FIG. 14 shows a top view of the clamp embodiment of FIG. 11.

FIG. 11 shows another embodiment wherein the spring traverses the line of craniotomy and is secured between separate attachments on the skull and flap. The spring is anchored on either side by a securing mechanism, such as a screw or nail or pin, and the spring extends in a generally oblique direction to the line of the craniotomy incision. The spring is tunneled through the bone (flap and vault) using an oblique path through the diploe (the diploe is the cancelous bone comprises between the externa and the intima laminae). FIGS. 12-14 provide exemplary illustrates of this embodiment.

Figure 15:
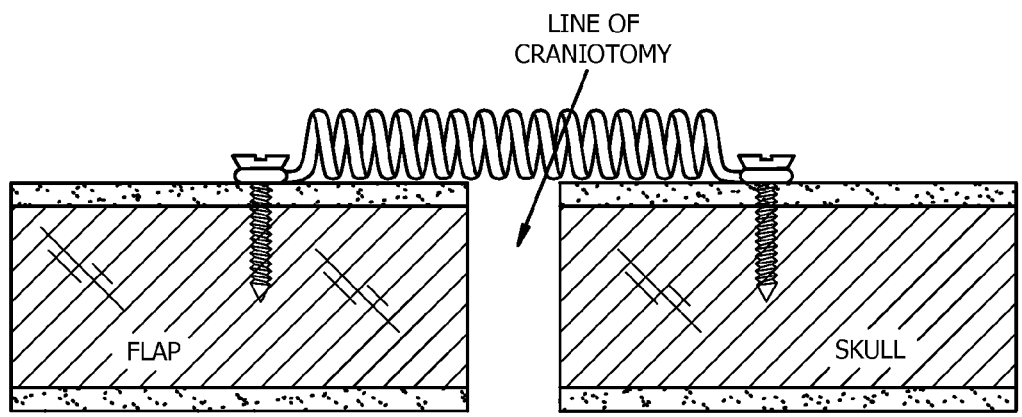
FIG. 15 provides a side view of one embodiment wherein the spring traverses the craniotomy cut in a generally horizontal manner above the externa lamina.
Figure 16:
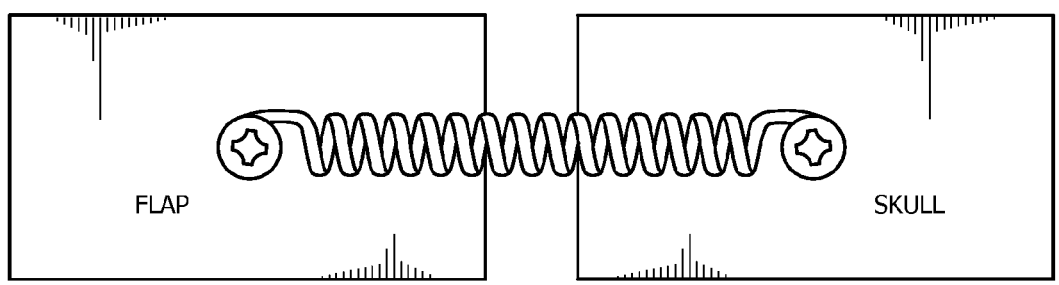
FIG. 16 shows a top view of the embodiment shown in FIG. 15.

FIG. 15 demonstrates an additional embodiment wherein the spring traverses the line of craniotomy and is secured between separate attachments on the skull and flap, although the spring extends in a generally horizontal direction across the line of the craniotomy incision. The spring is extended from the flap side to the vault side above the skull outside the lamina externa. In some embodiments, it may be needed to drill a hemi-cylindrical gutter in the externa lamina, and even maybe deeper within the diploe, in order to bury the spring for avoiding unaesthetic consequences as well as any soft tissue (skin) injury. FIG. 16 provides a top view of this particular embodiment. Alternatively, a rubber band may be used in lieu of the spring.

I. Method for Re-Attaching a Cranial Flap to the Skull Using One Embodiment

Positioning the clamps. The number of clamps is determined accordingly to the size and the shape of the flap, but at least three (3) clamps are preferably used in order to evenly distribute the pressure onto the flap. The size of each clamp is chosen accordingly to the bone thickness. The clamps are carefully installed on the dura mater, and their base is slid under the skull, within the extra-dural space, until the spring bumps against the bone (diploe of the skull). The bar 103 of each clamp is lined up with the line of craniotomy Re-positioning the flap. The bar of each clamp is properly positioned and line up with the line of craniotomy so that each bar does not hamper the placement of the flap.

Securely locking the clamp with the cap. The prehensile tool is successively engaged to each bars' notches, and then 90° rotated. The clamp is then securely fastened and the tool is removed. The maneuver is repeated for each clamp.

In case of re-intervention, the clamps can be easily removed by rotating an additional 90° which leads to re-align the bars with the line of craniotomy, and therefore frees the flap which can be lifted up again. Alternatively, the prehensile tool can be used, after being engaged in the lateral notches of the bar, to lift it up and expand the spring, which is then cut just under the bar.

II. Method for Re-Attaching a Cranial Flap to the Skull Using Another Embodiment Positioning the clamps. The number of clamps is determined accordingly to the size and the shape of the flap, but at least three (3) clamps must be used in order to evenly distribute the pressure onto the flap. Each spring mounted on its base is carefully installed on the dura mater, and slid within the extra dural space until the spring bumps against the diploe of the skull, so that only the hemi-bases are uncovered.

Re-positioning the flap. The flap is then repositioned, laying on each hemi-base. The springs are visible, sticking out from either the burr holes and/or the line of craniotomy.

Securely locking the clamp with the cap. The cap is spiraled down through the central aperture along the turns of the spring until its lower face grips into the lamina externa. Then, the unneeded stuck out portion of the spring is sectioned just out of the wide mouth horizontal plan, so that at least one (or two) turn(s) of the spring is (are) into the conical-shaped central recess contained between the outer wide mouth and the inner narrow end. The locking member is engaged into the conical-shaped central recess and then screwed in until it blocks the remaining turns of the spring.

Therefore, the clamp securely attaches the flap to the skull, the spring set at the adequate length is locked by the locking member and the assembly is completed.

In case of re-intervention, the clamps can be easily removed by unscrewing first the conical blocking member, then the cap. This removal frees the flap which can be lifted up again.

III. Method for Re-Attaching a Cranial Flap to the Skull Using Another Embodiment In some embodiments, a spring or other elastic material, such as a rubber band, is utilized to traverse the line of the craniotomy to secure the skull and flap portions. The spring, as an example, may traverse the line of the craniotomy in a generally horizontal direction relative to the cut, a generally vertical direction, or a generally oblique direction. The spring may be secured in the corresponding skull and flap regions in a direction that is perpendicular to the surface of the skull or the spring within the corresponding skull and flap regions may be positioned in a direction that is generally oblique to the line of craniotomy and/or surface of the skull.

To attach the cranial flap, a hole in the skull and flap portions may be generated in generally oblique angles compared to the line of craniotomy and/or surface of the skull, and the spring is inserted through these holes and secured with a screw or nail, for example.

From the foregoing disclosure and detailed description of certain preferred embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

REFERENCES

All patents and publications mentioned in the specification are indicative of the levels of those skilled in the art to which the invention pertains. All patents and publications are herein incorporated by reference to the same extent as if each individual publication was specifically and individually indicated to be incorporated by reference.

U.S. Pat. No. 6,258,091
U.S. Pat. No. 6,589,244
U.S. Pat. No. 5,707,373
U.S. Pat. No. 6,685,707

What is claimed is:

1. A cranial clamp for attaching a cranial flap to the skull, the cranial clamp comprising:
   a cap having an upper face and a lower face,
   the upper face including a conically-shaped central recess, having an outer mouth and an inner end disposed coaxially to a central unthreaded aperture, the outer mouth being wider than the inner end,
   the lower face including a plurality of radial teeth;
   an extension spring having a distal end and a proximal end, the distal end of the extension spring extending through the central unthreaded aperture;
   a locking member having an inner face, an outer face opposed to the inner face, and a threaded face adjacent to both the inner face and the outer face,
   the inner face being flat,
   the outer face including socket adapted to engage a fastening tool,
   the threaded face of the locking member engaging the conically-shaped central recess of the cap and the extension spring to secure the extension spring to the cap; and
   a base, the base being secured to the proximal end of the extension spring.

* * * * *